United States Patent [19]

Sun et al.

[11] Patent Number: 4,654,463

[45] Date of Patent: Mar. 31, 1987

[54] SKELETAL ISOMERIZATION OF OLEFINS OVER BROMIDED ALUMINAS

[75] Inventors: Hsiang-ning Sun, Media; Robert G. Gastinger, Brookhaven, both of Pa.

[73] Assignee: Atlantic Richfield Company, Los Angeles, Calif.

[21] Appl. No.: 791,042

[22] Filed: Oct. 24, 1985

[51] Int. Cl.$^4$ .............................................. C07C 5/27
[52] U.S. Cl. ............................................................ 585/671
[58] Field of Search ................................. 585/669, 671

[56] References Cited

U.S. PATENT DOCUMENTS 3,558,734  1/1971  Myers ................................... 585/671
3,635,931  1/1972  Davison ............................... 585/671
3,730,958  5/1973  Myers .................................. 585/671
4,405,500  9/1983  Muller et al. ........................ 585/669

FOREIGN PATENT DOCUMENTS 279954  4/1964  Australia ............................ 585/671

Primary Examiner—Asok Pal
Attorney, Agent, or Firm—Craig E. Larson

[57] ABSTRACT

A process for the skeletal isomerization of olefins wherein the olefins are contacted with a bromided alumina catalyst prepared by contacting alumina with a vapor selected from the group consisting of HBr, organic bromides, and Br$_2$/hydrocarbon mixtures.

9 Claims, 1 Drawing Figure

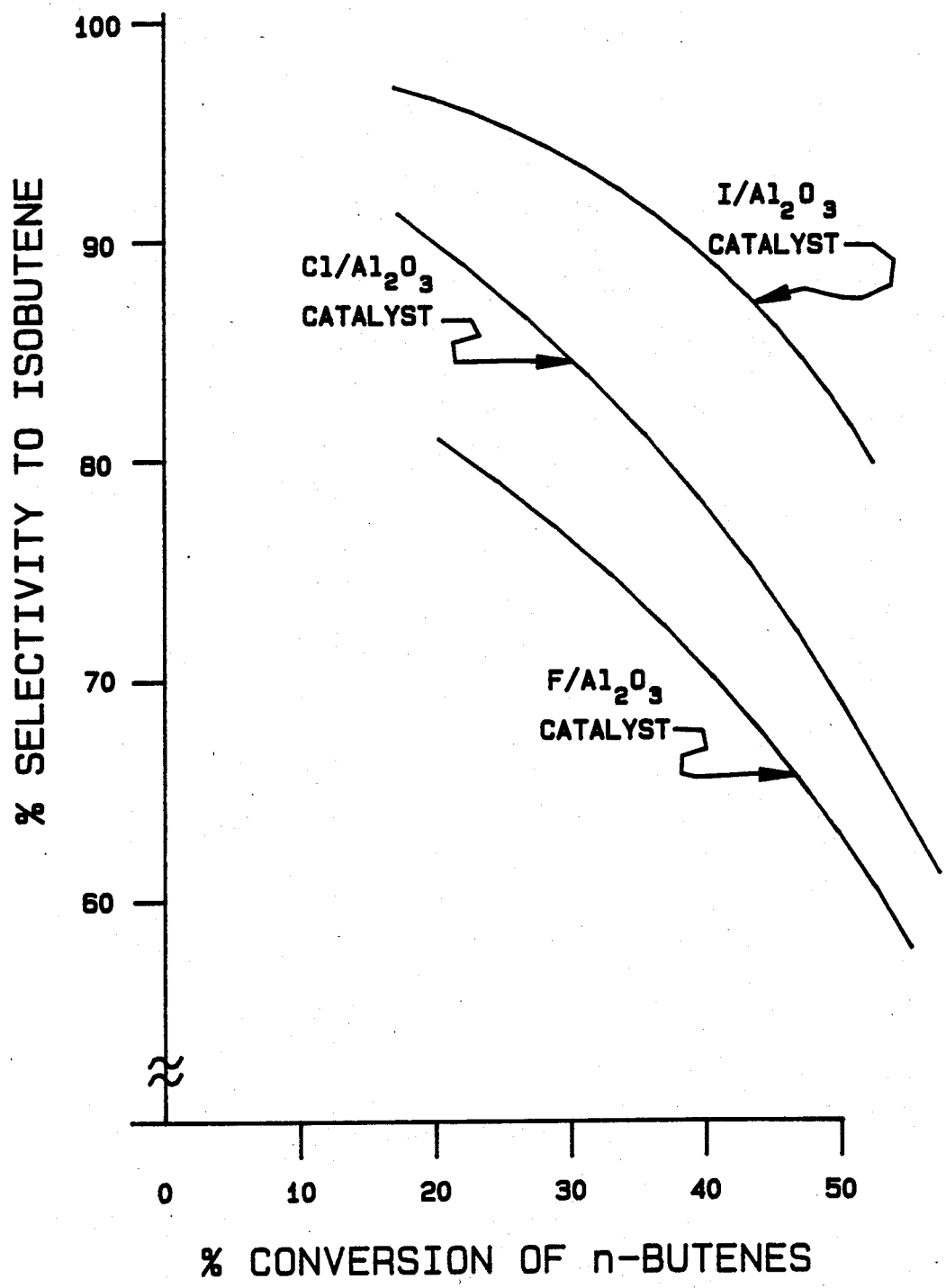

SKELETAL ISOMERIZATION OF OLEFINS OVER BROMIDED ALUMINAS

BACKGROUND OF THE INVENTION

This invention relates to skeletal isomerization of olefins, i.e., to the reorientation of the molecular structure in respect to the formation or elimination of side chains. This invention more particularly relates to the conversion of unbranched olefins into branched olefins having the same number of carbon atoms.

Skeletal isomerization of olefins is known to be accomplished by contacting unbranched or lightly branched olefins with acidic catalysts at elevated temperatures. The process is generally applicable to the isomerization of olefins having about 4 to about 20 carbon atoms and is especially applicable to olefins having about 4 to about 10 carbon atoms per molecule. The process may be used to form isobutene from normal butenes, methyl pentenes and dimethyl butenes from normal hexenes, and so forth.

Known skeletal isomerization catalysts include aluminas and halogenated aluminas, particularly F- or Cl-promoted aluminas. See Choudary, V. R., "Fluorine Promoted Catalysts: Activity and Surface Properties", *Ind. Eng. Chem., Prod. Res. Dev.*, 16(1), pp. 12–22 (1977) and U.S. Pat. Nos. 4,400,574 and 4,404,417. U.S. Pat. No. 3,558,734 teaches catalytic skeletal isomerization of hydrogen-diluted olefins in the presence of a halogen compound and/or water. The specification stresses the use of Cl- or F-impregnated alumina catalysts.

U.S. Pat. No. 3,663,453 teaches skeletal isomerization of olefins by contact with alumina promoted by a zirconyl halide. Zirconyl chloride is preferred, the order of increasing effectiveness of the halides being iodide, fluoride, bromide and chloride. The catalysts are prepared by impregnation techniques. The olefin feed preferably contains a halogen compound to maintain catalyst activity.

An object of this invention is an improved process for the skeletal isomerization of olefins, especially for the isomerization of n-butenes to form isobutene. A more specific object is an easily prepared, stable, active and selective isomerization catalyst and process for skeletal isomerization of olefins. Other objects and advantages of the invention will be apparent from the following description.

SUMMARY OF THE INVENTION

A process for the skeletal isomerization of olefins has now been found, which is characterized in that olefins having from about 4 to about 20 carbon atoms per molecule are contacted with a bromided alumina catalyst prepared by contacting alumina with a vapor selected from the group consisting of HBr, organic bromides and $Br_2$/hydrocarbon mixtures. The activity and selectivity of skeletal isomerization catalysts produced by vapor phase bromidation of alumina are superior to those produced liquid phase bromidation of alumina. The activity/selectivity characteristics and stability of the catalysts employed in the process of this invention are also superior to other halogenated aluminas such as chlorided or fluorided aluminas.

BRIEF DESCRIPTION OF THE DRAWING

The FIGURE is a plot of % conversion of n-butenes vs. % selectivity to isobutene for the results obtained in the following Example 13 and Comparative Example C and D.

DETAILED DESCRIPTION OF THE INVENTION

Any crystalline form of alumina may be employed to produce the catalyst used in the skeletal isomerization process of this invention, although gamma- and eta-aluminas are preferred. Amorphous alumina may also be employed. Preferably, the alumina support has a surface area of about 50 to about 700 m$^2$/gram (as measured by the BET method using $N_2$) and a pore volume of about 0.3 to about 1.8 cc/gram (as measured by mercury intrusion at 60,000 psig). The content of impurities which act to poison isomerization activity, such as alkali and alkaline earth metals, should be minimized.

Other inorganic oxides may be used with alumina in the catalyst of this invention. However, the catalyst should contain at least about 50 mole %, preferably at least about 70 mole %, of alumina. Examples of other inorganic oxides which can be used in combination with alumina are titania, silica, zirconia, thoria, hafnium oxide, zinc oxide, nickel oxide, phosphorus oxide, boron oxide, lanthanide oxides, gallium oxide, indium oxide, germanium oxide, tin oxide, bismuth oxide, arsenic oxide, molybdenum oxide, tungsten oxide, vanadium oxide and thallium oxide. The active alumina and such a compound may be a physical mixture or may be chemically bonded as in silica-alumina, zirconia-alumina, thoria-alumina and alumina-molybdena.

The catalyst should contain from about 0.05 to about 25 wt. % Br, preferably from about 0.5 to about 8 wt. % Br, based on the total catalyst weight. Deposition of Br on the alumina carrier is accomplished by contacting the carrier with a gas comprising vapors of selected Br sources. Bromine sources are selected from the group consisting of HBr, organic bromides, and $Br_2$/hydrocarbon mixtures. The bromine source selected will be vaporizable under bromidation conditions. Organic bromides suitable for use as a bromine source may be either aliphatic or aromatic bromides. Aliphatic bromides, especially aliphatic bromides having from 1 to 4 carbon atoms per molecule, are preferred. Examples are methyl bromide, ethylene dibromide and butyl bromides. When employing $Br_2$ as a bromine source, it has been found essential to add $Br_2$ in the presence of a hydrocarbon: adding $Br_2$ in the absence of hydrocarbon is not effective for the purposes of this invention. The hydrocarbon used with $Br_2$ is not narrowly critical and may be alkane, alkene, alkyne, aromatic, or mixtures thereof. Alkanes and alkenes having from about 1 to about 10 carbon atoms per molecular are preferred. A particularly suitable hydrocarbon is the isomerization feedstock of the method of this invention.

Vapor-phase bromidation of alumina carriers is accomplished by contacting the carrier with the bromine source (in the vapor phase) at temperatures within the range of about 100° to about 600° C. The temperatures of the contacting are not narrowly critical. Preferred contacting temperatures are within the range of about 250° to about 450° C. Contacting should be effected in a nonoxidizing atmosphere to prevent bromide oxidation. Addition of the bromine source in the vapor phase can be done either continuously or in pulses.

The skeletal isomerization process of this invention is carried out by contacting the feed with the catalyst, using any suitable contacting techniques, at temperatures at which skeletal isomerization of the feed olefins occurs. Feed should be maintained in the vapor phase during contacting. The temperature is preferably in the range of about 100° to about 650° C., more preferably about 300° to about 450° C. The gas hourly space velocity is not narrowly critical but will generally be within the range of about 10 to about 20,000 hr.$^{-1}$, preferably about 500 to about 10,000 hr.$^{-1}$. Any convenient pressure can be used, with the lowest practical pressure preferred in order to minimize side reactions such as polymerization. Preferred pressures are within the range of about 0.5 to about 300 psia, more preferably about 5 to about 25 psia.

The isomerization feedstock contains at least one alkene, preferably an alkene having from 4 to 12 carbon atoms per molecule, more preferably an alkene having from 4 to 10 carbon atoms per molecule. The alkene may have terminal or internal double bonds. Normal alkenes, especially normal butenes, are preferred feedstocks. Butene feedstocks may contain 1-butene, 2-butene or mixtures thereof. Examples of other normal alkenes which are useful feedstocks are 1- and 2-pentenes; 1-, 2- and 3-hexenes; 1-, 2- and 3-heptenes; and 1-, 2-, 3- and 4-octenes. The normal alkenes can be accompanied by other hydrocarbons, typically other hydrocarbons having the same carbon atoms as the alkene feed. In the case of normal butenes, examples of other hydrocarbons are normal-butane and isobutane.

Particular feedstocks contemplated for use in the present process are fractions containing n-butenes, optionally mixed with isobutene, isobutane and n-butane. Such fractions are commonly produced in petrochemical plants and refineries and as, for example, after the separation of 1,3-butadiene from a C$_4$ cut or in the cracking of waxy distillates. Isobutene present is in such fractions is commonly converted by catalytic reaction with methanol to produce methyl tertiary butyl ether ("MTBE"). MTBE is separated by distillation, leaving a residual C$_4$ cut. Isobutene present in such fractions may also be oligomerized to produce oligomers which are then separated, again leaving a residual C$_4$ cut. In either MTBE production or oligomerization, a mixture of n-butenes, n-butane and isobutane remains in the residual material. It is desirable to produce additional isobutene from the residual material and return the isobutene for further conversion by the reactions mentioned above.

The olefinic feed stream can contain inert gaseous diluents (e.g. paraffins, N$_2$, etc.). The diluent may be present in any desired proportion, e.g., up to about 95 wt. % of the olefinic feed stream.

Selection of isomerization conditions is dependent on olefins to be isomerized. In general, lower temperatures are used for feeds containing larger olefin molecules.

Maintenance of catalyst activity may be enhanced by addition, either continuously or intermittently, of small amounts of a bromine source to the feed stream. Such materials are preferably added to the feed in amounts varying from about 10 to about 10,000 ppm (wt., expressed as Br) more preferably about 100 to about 1000 ppm. Use of Br compounds, as opposed to Cl or F compounds, minimizes corrosion of equipment. Use of aliphatic bromides is particularly effective.

The catalysts are regeneratable by heating in an oxygen-containing gas at temperatures ranging from about 200° to about 700° C. and treating the oxidized catalyst with a bromine source as described above.

The invention is further illustrated by reference to the following examples. All performance data reported in the examples were obtained after catalyst stabilization (usually one to three hours after starting the reaction).

EXAMPLE I

Twenty-five ml. of alumina was placed in a tubular reactor and treated with a vapor formed by injection of 50 ml. of anhydrous HBr into a stream of N$_2$ at 400° C. After being purged with N$_2$ for five minutes, a 1:1 mixture of 1-butene and 2-butenes was passed over the catalyst. At 440° C., 905 GHSV and 0 psig, 33.2% conversion of the butene feed was observed. Product selectivities (wt. %) were: 0.1% C$_2$, 2.0% C$_3$, 0.5% isobutane/n-butane, 86.5% isobutene, and 10.9% C$_5$+ hydrocarbons.

EXAMPLE 2

Twenty-five ml. of alumina was placed in a tubular reactor and treated as described in Example 1. The catalyst was contacted with 1-butene. At 450° C., 1250 GHSV and 750 torr pressure, 29% conversion of the butene feed was observed. Product selectivities (wt. %) were: 0.1% C$_2$, 1.2% C$_3$, 0.3% isobutane/n-butane, 91.4% isobutene, and 7.0% C$_5$+ hydrocarbons.

EXAMPLE 3

Twenty-five ml. of alumina was placed in a tubular reactor and treated as described in Example 1. The catalyst was contacted with a feed containing 375 torr of 1-butene and 375 torr of N$_2$. At 450° C. and 450 GHSV (based on 1-butene), 37.5% conversion of the butene feed was oberved. Product selectivities (wt. %) were: 1.1% C$_1$–C$_3$ hydrocarbons, 0.4% isobutane/n-butane, 88.3% isobutene, and 10.2% C$_5$+ hydrocarbons.

EXAMPLE 4

Fifteen ml. of alumina was placed in a tubular reactor and treated with a vapor formed by injection of 2 ml. of liquid n-butyl bromide into N$_2$ at 415° C. After being purged with N$_2$ for five minutes, a 1:1 mixture of cis-butene-2 and trans-butene-2 was passed over the catalyst. At 450° C., 1100 GHSV, and about atmospheric pressure, 40.1% conversion of the butene feed was observed. Product selectivities (wt. %) were: 3.8% C$_1$–C$_3$ hydrocarbons, 0.8% isobutane/n-butene, 82.0% isobutene, and 13.5% C$_5$+ hydrocarbons.

COMPARATIVE EXAMPLE A

This example and Comparative Example B demonstrate the importance of vapor-phase bromidation to the method of this invention.

A catalyst was prepared by impregnating alumina with an aqueous solution of NH$_4$Br. After dyring at 110° C. for 1 hour, the catalyst was calcined at 500° C. for 5 hours. The catalyst contained 2.5 wt. % Br. A feed of n-butenes was passed over the catalyst. At 425° C., 1200 GHSV and 0 psig, the conversion of the butene feed was less than 2%.

COMPARATIVE EXAMPLE B

Comparative Example A was repeated but the calcination step was omitted. At 425° C., 1200 GHSV, and 0 psig, 13% of the butene feed was converted. Product selectivities were 1.7% C$_3$ hydrocarbons, 0.8% isobutane/n-butane, 89.3% isobutene and 8.3% C$_5$+ hydrocarbons.

EXAMPLES 5-12

These examples were prepared following the general procedure of Example 4. Addition of the bromide source was either continuous (c) or in a pulse (p). The bromide concentration in the butene feed for the continuous mode was 150-350 ppm (wt., as Br). The quantity of bromide used in the pulse mode was equivalent to 0.5-25 wt. % of the support. The amounts of bromide were chosen to give the desired activities. Other reaction parameters are shown in Table I. The products were analyzed regularly. The reported performance data were obtained after the catalysts have stabilized, (usually one to three hours after the reaction has started).

TABLE 1

| Example | 5 | 6 | 7 | 8 | 9 | 10 | 11 | 12 |
|---|---|---|---|---|---|---|---|---|
| Br source[1] | n-BuBr | n-BuBr | MeBr | MeBr | HBr | n-BuBr | heavies | bromohydrin |
| Br quantity[2] | 25 ml. (gas) | 210 ppm | 120 ppm | 450 ppm | 75 ml. (gas) | 45 ml. (gas) | 7.5 ml. (liquid) | 0.5 ml. (liquid) |
| Addition[3] Method | P | C | C | C | P | P | P | P |
| Feed[4] | B-1 | B-1 | B-2 | B-2 | B-1 | B-1/B-2 | B-1/B-2 | B-1 |
| Temp. (F°) | 840 | 838 | 845 | 797 | 797 | 784 | 775 | 835 |
| GHSV | 1050 | 1035 | 1075 | 1330 | 1370 | 985 | 1090 | 750 |
| % Conv. | 31.9 | 29.9 | 20.9 | 50.5 | 51.2 | 39.5 | 37.2 | 31.0 |
| Wt. % Sel. | | | | | | | | |
| $C_1$–$C_3$ | 3.48 | 3.28 | 14.9 | 6.29 | 9.04 | 4.20 | 3.56 | 3.89 |
| isobutane/n-butane | 0.53 | 0.23 | trace | 1.97 | 2.18 | 1.70 | 0.53 | 0.77 |
| isobutene | 88.0 | 89.9 | 92.4 | 67.2 | 68.4 | 77.6 | 80.1 | 88.1 |
| $C_5+$ | 8.05 | 6.58 | 6.09 | 24.6 | 20.4 | 19.0 | 15.9 | 7.24 |

[1] "n-BuBr": n-butyl bromide; "MeBr": methyl bromide; "heavies": $C_5+$ fraction recycled from Example 8.
[2] Br quantity is shown as total volume of Br source added in pulse mode. Br quantity is shown as ppm (wt., as Br) added with feed in continuous mode.
[3] "P" pulse; "C": continuous.
[4] "B-1": 1-butene; "B-2": 1:1 mixture of cis- and trans- butenes -2; "B-1/B-2": 1:1 mixture of 1-butene and 2-butenes.

EXAMPLE 13 AND COMPARATIVE EXAMPLES C AND D

A comparative study between the bromided catalysts of this invention and chlorided and fluorided catalysts was done.

The bromided catalyst (Example 13) was prepared as described above in Example 14. During performance runs, n-butyl bromide was continuously added with 1-butene feed at concentrations ranging from 50 to 350 ppm (wt., as Br).

To prepare the chlorided alumina catalyst (Comparative Example C), 15 ml. of alumina was placed in a tubular reactor. After purging with $N_2$, a 1-butene feed was introduced into the reactor. A pulse of 24 ml. of gaseous methyl chloride was added to the feed at about 427° C. and about 0 psig. During performance runs, methyl chloride was continuously added with 1-butene feed at concentrations ranging from 50 to 500 ppm (wt., as Cl).

The fluorided alumina catalyst (Comparative Example D) was prepared by impregnating alumina with aqueous $NH_4F$ solution, drying at 120° C. for five hours, and calcining at 550° C. for four hours. The final catalyst composition contained 1.0 wt. % F.

Isomerization of 1-butene was performed over each of the foregoing catalysts at 400°-450° C., 0 psig, and 7-12 hr.$^{-1}$ LHSV (liquid hourly space veocity). The reaction conditions and (in Example 13 and Comparative Example C) Cl and Br concentrations in the 1-butene feed were adjusted to give the desired conversions. Results obtained for each catalyst are shown in the FIGURE as a plot of conversion vs. selectivity.

What is claimed is:

1. A process for the skeletal isomerization of olefins having from about 4 to about 20 carbon atoms per molecule which comprises contacting said olefins in the absence of hydrogen with a bromided alumina catalyst prepared by contacting alumina with a vapor selected from the group consisting of HBr, organic bromides, and $Br_2$/hydrocarbon mixtures.

2. The process of claim 1 wherein said vapor is an organic bromide selected from the group consisting of aliphatic bromides and aromatic bromides.

3. The process of claim 1 wherein said vapor is aliphatic bromide.

4. The process of claim 3 wherein the vapor is an aliphatic bromide having from 1 to about 4 carbon atoms per molecule.

5. The process of claim 1 wherein the vapor is HBr.

6. The process of claim 1 wherein the vapor is a $Br_2$/hydrocarbon mixture.

7. The process of claim 1 wherein olefins fed to the process has from about 4 to about 10 carbon atoms per molecule.

8. The process of claim 1 wherein normal butenes are isomerized to produce isobutene.

9. The method of claim 1 wherein alumina is contacted with said vapor in a nonoxidizing atmosphere.

* * * * *